(12) United States Patent
Chaton et al.

(10) Patent No.: US 6,884,582 B1
(45) Date of Patent: Apr. 26, 2005

(54) METHOD AND DEVICE FOR DETECTING A MOLECULAR RECOGNITION REACTION

(75) Inventors: Patrick Chaton, Theys (FR); Ludovic Poupinet, Seyssinet (FR); Frédéric Ginot, Voreppe (FR); Armelle Novelli Rousseau, Seyssins (FR)

(73) Assignees: Commissariat a l'Energie Atomique, Paris (FR); Biomerieux SA., Marcy L'etoile (FR)

( * ) Notice: Subject to any disclaimer, the term of this patent is extended or adjusted under 35 U.S.C. 154(b) by 372 days.

(21) Appl. No.: 10/089,164

(22) PCT Filed: Sep. 29, 2000

(86) PCT No.: PCT/FR00/02703

§ 371 (c)(1),
(2), (4) Date: Mar. 27, 2002

(87) PCT Pub. No.: WO01/23867

PCT Pub. Date: Apr. 5, 2001

(30) Foreign Application Priority Data

Sep. 30, 1999 (FR) .............................................. 99 12229

(51) Int. Cl.[7] .......................... C12Q 1/68; C07H 21/02; G01N 21/29; G01N 21/27
(52) U.S. Cl. ...................... 435/6; 536/23.1; 422/82.05; 422/82.09
(58) Field of Search ............................ 435/6; 536/23.1; 422/82.05, 82.09

(56) References Cited

U.S. PATENT DOCUMENTS 5,874,213 A    2/1999   Cummin et al.
6,537,801 B1 * 3/2003   Ida et al. ................. 435/287.2

FOREIGN PATENT DOCUMENTS

WO    WO 00/20861    *    4/2000

OTHER PUBLICATIONS

Milofsky et al, "Natie fluorescence detection of nucleic acids and DNA restriction fragments in capillary electrophoresis", Analytical Chemistry (1993) 65:153–157.*

K. Adelhelm, et al. "Development of a Sensitive Detection System Based on the Photothermal Effect for Biomolecular Interaction Studies," Biomedical Optoelectronics in Clinical Chemistry and Biotechnology, Sep. 14, 1995, vol. 2629, pp. 325–333.

Tamao Odake, et al., "High–Speed Separation Using Minaturized Slab Gel and High Spatial Resolution Detection by Thermal Lens Microscope," Proceedings of the 1998 Thermal Therapy, Laser Welding and Tissue Interaction, Sep. 9, 1998, SPIE vol. 3565, pp. 126–133.

Takehiko Kitamori, "Chemistry and Analysis in Integrated Chemistry Lab on Chip," Digest of Papers Nanotechnology, 1999, pp. 70–71.

* cited by examiner

*Primary Examiner*—Jeffrey Fredman
(74) *Attorney, Agent, or Firm*—Oblon, Spivak, McClelland, Maier & Neustadt, P.C.

(57) ABSTRACT

The present invention relates to a method for detection of a molecular recognition reaction without labelling and a device for using this method.

This invention concerns the general field of detection and analysis of molecular recognition between a first and a second molecule, for example a biological molecule.

The method of the present invention consists of the detection of the molecular recognition by a photothermal method.

26 Claims, 3 Drawing Sheets

SEQUENCE LISTING

<160> NUMBER OF SEQ ID NOS: 24

<210> SEQ ID NO 1
<211> LENGTH: 18
<212> TYPE: DNA
<213> ORGANISM: Artificial Sequence
<220> FEATURE:
<223> OTHER INFORMATION: Synthetic DNA

<400> SEQUENCE: 1
ttcgacagcg acgtgggg                                                 18

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

```
<400> SEQUENCE: 2
tatgaaactt atggggatac                                                    20

<210> SEQ ID NO 3
<211> LENGTH: 16
<212> TYPE: DNA
<213> ORGANISM: Artificial Sequence
<220> FEATURE:
<223> OTHER INFORMATION: Synthetic DNA

<400> SEQUENCE: 3
gatacttcta tcacca                                                        16

<210> SEQ ID NO 4
<211> LENGTH: 15
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (13)..(13)
<223> OTHER INFORMATION: n = inosine

<400> SEQUENCE: 4
gagcagaanc ggncc                                                         15

<210> SEQ ID NO 5
<211> LENGTH: 15
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (12)..(12)
<223> OTHER INFORMATION: n = inosine

<400> SEQUENCE: 5
ctggaagacg ancgg                                                         15

<210> SEQ ID NO 6
<211> LENGTH: 18
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (5)..(5)
<223> OTHER INFORMATION: n = inosine
<220> FEATURE:
<221> NAME/KEY: misc_feature
<222> LOCATION: (7)..(7)
<223> OTHER INFORMATION: n = inosine
<220> FEATURE:
<221> NAME/KEY: misc_feature
<222> LOCATION: (10)..(10)
<223> OTHER INFORMATION: n = inosine
<220> FEATURE:
<221> NAME/KEY: misc_feature
<222> LOCATION: (13)..(13)
<223> OTHER INFORMATION: n = inosine
<220> FEATURE:
<221> NAME/KEY: misc_feature
<222> LOCATION: (15)..(15)
```

```
<223> OTHER INFORMATION: n = inosine
<220> FEATURE:
<221> NAME/KEY: misc_feature
<222> LOCATION: (17)..(18)
<223> OTHER INFORMATION: n = inosine

<400> SEQUENCE: 6
agcanangcn ggncnann                                               18

<210> SEQ ID NO 7
<211> LENGTH: 18
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (11)..(13)
<223> OTHER INFORMATION: n = inosine
<220> FEATURE:
<221> NAME/KEY: misc_feature
<222> LOCATION: (15)..(15)
<223> OTHER INFORMATION: n = inosine

<400> SEQUENCE: 7
cagaggcgng nnncnctg                                               18

<210> SEQ ID NO 8
<211> LENGTH: 15
<212> TYPE: DNA
<213> ORGANISM: Artificial Sequence
<220> FEATURE:
<223> OTHER INFORMATION: Synthetic DNA

<400> SEQUENCE: 8
gcctagcgcc gagta                                                  15

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9
tggcagctta agtttgaa                                               18

<210> SEQ ID NO 10
<211> LENGTH: 16
<212> TYPE: DNA
<213> ORGANISM: Artificial Sequence
<220> FEATURE:
<223> OTHER INFORMATION: Synthetic DNA

<400> SEQUENCE: 10
tactctacgt ctgagt                                                 16

<210> SEQ ID NO 11
<211> LENGTH: 17
<212> TYPE: DNA
<213> ORGANISM: Artificial Sequence
<220> FEATURE:
<223> OTHER INFORMATION: Synthetic DNA

<400> SEQUENCE: 11
```
cagcctaaga gggagtg                                              17

<210> SEQ ID NO 12
<211> LENGTH: 18
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n = inosine
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (11)..(11)
<223> OTHER INFORMATION: n = inosine

<400> SEQUENCE: 12
naggtngaca ncgtgtgc                                             18

<210> SEQ ID NO 13
<211> LENGTH: 15
<212> TYPE: DNA
<213> ORGANISM: Artificial Sequence
<220> FEATURE:
<223> OTHER INFORMATION: Synthetic DNA

<400> SEQUENCE: 13
ggaggaggtt aagtt                                                15

<210> SEQ ID NO 14
<211> LENGTH: 14
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (10)..(10)
<223> OTHER INFORMATION: n = inosine

<400> SEQUENCE: 14
ctctacgggn gagt                                                 14

<210> SEQ ID NO 15
<211> LENGTH: 16
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(14)
<223> OTHER INFORMATION: n = inosine

<400> SEQUENCE: 15
ccgggtggac aacnac                                               16

<210> SEQ ID NO 16
<211> LENGTH: 27
<212> TYPE: DNA
<213> ORGANISM: Artificial Sequence
<220> FEATURE:
<223> OTHER INFORMATION: Synthetic DNA

```
<400> SEQUENCE: 16
ccggatcctt cgtgtcccca cagcacg                                27

<210> SEQ ID NO 17
<211> LENGTH: 19
<212> TYPE: DNA
<213> ORGANISM: Artificial Sequence
<220> FEATURE:
<223> OTHER INFORMATION: Synthetic DNA

<400> SEQUENCE: 17
tcgccgctgc actgtgaag                                         19

<210> SEQ ID NO 18
<211> LENGTH: 15
<212> TYPE: DNA
<213> ORGANISM: Artificial Sequence
<220> FEATURE:
<223> OTHER INFORMATION: Synthetic DNA

<400> SEQUENCE: 18
gagcagaagc gggcc                                             15

<210> SEQ ID NO 19
<211> LENGTH: 15
<212> TYPE: DNA
<213> ORGANISM: Artificial Sequence
<220> FEATURE:
<223> OTHER INFORMATION: Synthetic DNA

<400> SEQUENCE: 19
ctggaagacg agcgg                                             15

<210> SEQ ID NO 20
<211> LENGTH: 18
<212> TYPE: DNA
<213> ORGANISM: Artificial Sequence
<220> FEATURE:
<223> OTHER INFORMATION: Synthetic DNA

<400> SEQUENCE: 20
agcagaggcg ggccgagg                                          18

<210> SEQ ID NO 21
<211> LENGTH: 18
<212> TYPE: DNA
<213> ORGANISM: Artificial Sequence
<220> FEATURE:
<223> OTHER INFORMATION: Synthetic DNA

<400> SEQUENCE: 21
cagaggcggg ccgcggtg                                          18

<210> SEQ ID NO 22
<211> LENGTH: 18
<212> TYPE: DNA
<213> ORGANISM: Artificial Sequence
<220> FEATURE:
<223> OTHER INFORMATION: Synthetic DNA

<400> SEQUENCE: 22
caggtggaca ccgtgtgc                                          18

<210> SEQ ID NO 23
<211> LENGTH: 14
```

-continued

```
<212> TYPE: DNA
<213> ORGANISM: Artificial Sequence
<220> FEATURE:
<223> OTHER INFORMATION: Synthetic DNA

<400> SEQUENCE: 23
ctctacgggt gagt                                                      14

<210> SEQ ID NO 24
<211> LENGTH: 16
<212> TYPE: DNA
<213> ORGANISM: Artificial Sequence
<220> FEATURE:
<223> OTHER INFORMATION: Synthetic DNA

<400> SEQUENCE: 24
ccgggtggac aactac                                                    16
```

METHOD AND DEVICE FOR DETECTING A MOLECULAR RECOGNITION REACTION

TECHNICAL FIELD OF THE INVENTION

The present invention relates to a method for detecting a molecular recognition reaction without any labelling, and to a device for implementing this method.

This invention relates to the general field of detection and analysis of a molecular recognition between a first and second molecule, for example in molecular biology.

According to the invention, molecular recognition may be defined as a specific interaction between more or less complex molecules, leading to a sufficiently stable bond of both molecules so that the molecules may be detected as bound molecules. For example, this may be a hybridization of nucleic acids (DNA and/or RNA), with a recognition reaction of the type antigen/antibody, an interaction of the protein/protein type, an interaction of the enzyme/substrate type, etc . . . The molecules relevant to the present invention are therefore those which are involved in the aforementioned interactions.

With the method of the present invention, this type of molecular recognition wherein one of the two molecules is fixed on a solid support, may be detected by detecting a change in absorption by a photothermal method.

This method notably finds application in the detection of the hybridization of nucleic acids on a solid support, in an aqueous medium or in air, for example within the framework of a screening or of a detection of hybridization on a biochip.

STATE OF THE ART

For example, detection of nucleic acid hybridization is generally performed by means of labelling with a fluorescent molecule. However, this type of detection requires the use of several chemical reagents, and leads to a high cost and a long processing period. Further, techniques which utilize fluorescence are not always very accurate. Finally, at least one molecule is modified by the labelling, this may affect the molecular recognition reaction.

Also, other methods have been suggested, for example optical methods consisting in detecting thickness or index changes in a sample, for example by ellipsometry, photogoniometry or by resonance methods.

However, in the case of oligonucleotides on a solid support, for example, the formed layers are ultrafine, from a few angstroms to a few nanometers thick, so that the detection of thickness or index changes requires extremely sensitive and expensive laboratory apparatuses.

DISCUSSION OF THE INVENTION

Specifically, the object of the present invention is to provide a new detection technique without any labelling, for a molecular recognition reaction between a first molecule, a so-called capture molecule, fixed on a solid support, and a second molecule, a so-called target molecule, present in a solution to be tested.

The method of the invention is characterized in that the detection is performed by a photothermal method.

According to the invention, the recognition reaction as well as the first and second molecules may be the aforementioned ones.

When the first and the second molecules are nucleic acid molecules, the method of the invention, for example, may comprise the: following steps:

- fixation of the first nucleic acid molecule on a solid support,
- contacting of the first molecule of nucleic acid fixed on the solid support with a solution to be tested, suspected of comprising the second nucleic acid molecule, the latter being capable of hybridizing to said first molecule, the contacting being carried out under conditions favourable to said hybridization,
- washing of the solid support in order to isolate a detection sample consisting of said first molecule fixed on the support and optionally of said second molecule hybridized on the first molecule, and
- measurement of the absorption of the sample by a photothermal method.

In addition, the method of the present invention may comprise a step for comparing the measurement of the absorption of the predefined measurement sample, with that of a control sample, a so-called calibration sample, the absorption of which is a known measure.

The first molecule, fixed on the support, may also be called a capture molecule and the second molecule, present in the solution to be tested, may also be called a target molecule. It may also be called a "probe" when this is a DNA molecule fixed on the support.

It is important to note that thin nucleic acid layers whether hybridized or not, are usually considered as non-absorbing. This is notably described in "Ellipsometric and interferometric characterization of DNA probes immobilized on a combinational assay", Gray et al., Langmuir 1997, 13, 2833–2842.

In spite of this, the present inventors were interested in photothermal methods applied to the detection and analysis of a molecular recognition reaction. All these methods have in common, the excitation of the sample, the absorption of which should be measured by a light source, called the pump beam, generally a laser. A portion of the incident light energy is absorbed by the sample. The proportion of absorbed energy is set by the absorption spectrum of the sample and the emission spectrum of the excitation source. A portion of the absorbed energy is transformed into heat. The remainder may be radiated or give rise to fluorescence or to a chemical reaction, for example. The heat induces a change in temperature in the absorbing medium and in the adjacent media, the change in temperature may also be expressed by a change in density and therefore in index, or by a change in pressure, or by the occurrence of an acoustical wave. The rise in temperature due to absorption is generally inhomogeneous, and therefore gives rise to an index gradient of the analyzed medium and of the adjacent media, whereby the density of the media is made inhomogeneous by the rise in temperature.

Photothermal methods consist in measuring the effects induced by the absorption.

The inventors have demonstrated that among the photothermal methods, the photothermal deflection method and the thermal lens method may for example be used according to the present invention.

The photothermal deflection method is a method which consists in measuring the deviation of a light beam, called the probe beam, passing in the area where the index gradient is to be found. In other words, it consists in measuring the deviation of the probe beam due to the heating of an absorbing sample via the pump beam. This photothermal deflection technique has been applied to surface analysis such as absorption mapping, thermal parameter imaging, but never for detecting molecular recognition as defined above.

The thermal lens method as to itself consists in measuring the change in the focussing of a light beam passing in the area where the index gradient is to be found.

A full presentation of photothermal methods may be found for example in the textbook "Photothermal Spectroscopy Methods for Chemical Analysis, S. E. Bialkowski, vol. 134 in Chemical Analysis: a Series of Monographs on Analytical Chemistry and its Applications, Wiley".

According to the method of the invention, the solid support may be defined as a support on which the first molecule may be chemically fixed directly or indirectly. Preferably, the support has low absorption as compared to that of the sample placed at its surface so as not to interfere with photothermal detection. Moreover, it preferably has low thermal conductivity since a too large conductivity of the support induces wide distribution of the heat, therefore a lowering of the temperature gradient and a lowering of the detected signal.

According to the invention, this support may for example be a support which is used in the manufacturing of DNA chips, for example a silica, glass or plastic support. It is also possible to work with semiconductors, by coating their surface with dielectric layers in order to improve the signal to noise ratio.

According to the invention, the first so-called capture molecule is fixed on the support. This fixation of the first molecule on the support may be achieved by conventional chemical reactions well known to one skilled in the art, and selected according to the support, the molecule to be fixed and the bond's strength properties which are desired for the targeted application.

This fixation may be direct or indirect.

Documents 1 to 10 mentioned below are detailed in the references at the end of this specification.

For example, according to the invention, when the support is a silica support, a functionalization treatment of the silica support may be performed before fixing the first molecule, so as to modify the surface of the support in order to fix reactive chemical groups thereon, which will allow the first molecule to be fixed. Such a treatment is described in Example 1 below, but a great number of other examples will be found in the specialized literature, such as Pease et al. (Document 6), Guo et al. (Document 4), Maskos et al. (Document 6) etc. As stated earlier, silica is not the only possible support and each support will undergo the surface treatment which is suitable for it. To illustrate this on a polypropylene film, for example, reference will be made to Matson et al. (Document 7).

The reactive chemical groups are generally amine groups such as those mentioned in Guo et al. (Document 4) or carboxylic groups such as those mentioned in Kohsaka et al. (Document 5), or epoxy groups such as those mentioned in Maskos et al. (Document 6), for which commercial coupling agents exist, which are efficient and easy to use (see the Pierce catalog, for example).

Covalent coupling is not the only way for fixing the first molecule on its support. Passive adsorption widely used for fixing antibodies on polystyrene reaction wells or on microbeads such as described in Elaissari et al. (Document 3), is often very effective, also see Balladur et al. (Document 1). More recent fixation techniques may also be contemplated, such as the formation of a Langmuir-Blodgett film in which are included lipid chains onto which the first molecule has been coupled chemically, see Noy et al. (Document 8); and Cornell et al. (Document 2), or further the metal-chelate method, see Porath et al., 1975 (Document 10).

According to the invention, when the first molecule is fixed on the support, the following steps may be the aforementioned contacting step and washing step.

According to the invention, the contacting step is of course, performed under conditions which are favorable to said hybridization, i.e., and obviously for one skilled in the art, at a suitable pH, at a suitable temperature and in a suitable solution for enabling hybridization of nucleic acids. This solution is the solution to be tested.

According to the invention, the step for washing the support notably has the purpose of removing the molecules in the solution which have not reacted with the recognition molecules on the support, i.e. in the above example, the nucleic acid molecules of the solution which are not hybridized to the nucleic acid molecules fixed on the support. A strong background noise level which would be generated by said molecules non-hybridized and not bound to the support may thus be avoided during the measurement.

Of course, the washing of the support on which are fixed the molecules, should be a mild wash which does not denaturate the nucleic acids involved in the hybridizations, does not destroy said formed hybridizations and does not release the first molecules fixed on the support. A washing example is given in the example below. With this washing step, it is possible to obtain the measurement sample used for measuring the absorption by the selected photothermal method.

According to the method of the invention, when the selected photothermal method is a photothermal deflection method, the sample comprising nucleic acids for example, is illuminated with a light beam called a pump beam and the absorption of the pump beam by the sample is detected by refraction or reflection of a probe beam.

The pump beam may for example be a pulsed laser or an intensity-modulated continuous laser. Preferably, it has an emission wavelength in the absorption range of the sample, for example in that of nucleic acids when the purpose is to detect hybridization of nucleic acids.

According to the invention, the probe beam preferably has a wavelength which is neither absorbed by the present substrate nor by the present molecules.

According to the invention, the pump beam may be a beam from a laser selected from a 275 nm continuous argon laser or a quadruple YAG laser with a wavelength of 266 nm. The pump beam may also be provided by a polychromatic source, for example, a mercury vapor lamp, if the emission spectrum of the source and its intensity provides sufficient signal for the detection.

The probe beam is directed to near the sample portion illuminated by the pump beam. Moreover, the probe beam may be identical with, or different from the pump beam. The probe beam is preferably a laser beam, for example one from a 633 nm helium laser.

The relative position of the probe and pump beams define the configuration used. For example, the probe beam may cross one or more of the following media: the sample, for example the oligonucleotides, the solid support or the surrounding medium, for example a liquid or air.

The orientation of the probe beam with respect to the pump beam, may be selected at will, for example depending on the mechanical congestion and/or for optimizing the sensitivity by seeking maximum absorption according to the incidence angle.

According to the invention, the probe and pump beams may cross each other.

Figure 1:
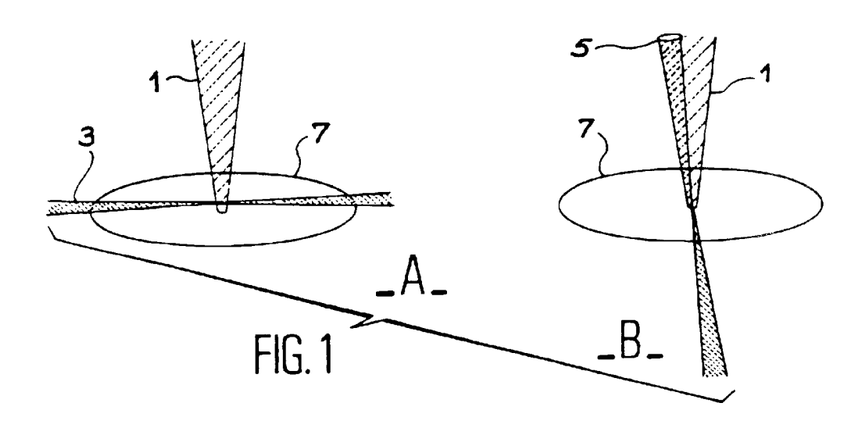
FIG. 1 is a schematic illustration of the transverse (FIG. 1a) and colinear (FIG. 1b) configurations of the pump and probe beams in a detection of photothermal deflection according to the method of the invention.

According to the invention, the probe and pump beams may be positioned in a transverse configuration or in a substantially colinear configuration. In the transverse configuration, the probe and pump beams cross each other, and are perpendicular to each other. This configuration is schematically illustrated in the appended FIG. 1a. In the substantially colinear configuration, the pump and probe beams cross each other, but are nearly colinear. The appended FIG. 1b is a schematic illustration of the colinear configuration.

In these figures, reference 1 shows the pump beam, reference 3 the probe beam in the transverse configuration, reference 5 the probe beam in the substantially colinear configuration and reference 7 the measurement sample positioned on the solid support.

Reflection or refraction of the probe beam may be detected by means of a multicomponent photodiode, for example by a detector with two or four quadrants, by an array or a matrix, or by means of a single photodiode, either partly covered by a cover or knife, or only receiving a portion of the probe beam.

In the case of a single photodiode, another detector may be required in order to dissociate the changes in absorption of the sample, from the possible power changes of the pump beam.

Figure 2:
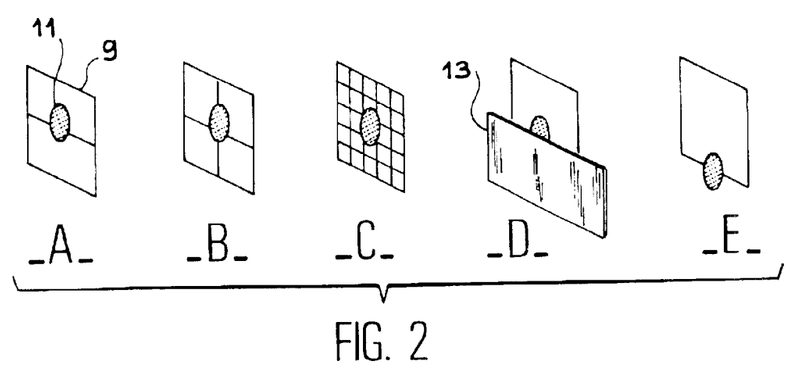
FIG. 2 is a schematic illustration of different configurations for detecting the deviation of the probe beam.

FIG. 2 is a schematic illustration of various configurations for detecting the deviation of the probe beam. In this figure, -A- schematically illustrates a bi-quadrant detector 9 and a spot 11 formed by the probe beam on the detector, -B- illustrates a four-quadrant detector, -C- illustrates a matrix detector, -D- illustrates a single photodiode partly covered with a cover 13, and -E- illustrates an off-axis photodetector.

In order to achieve sufficient sensitivity, deflection of the probe beam induced by the absorption of a portion of the pump beam by the sample, for example by oligonucleotides, is preferably distinguished from the parasitic changes due to the environment, such as temperature changes in the laboratory. For this, the pump beam may be marked in time either by modulation if it is a continuous beam, or by its pulsed operation. By controlling the modulation frequency and the possibility of obtaining a reference signal, the deflection due to the heating generated by partial absorption of the pump beam may be detected preferentially.

Whatever the configuration of the beams used, the obtained information is local and relates to an area around the pump beam's impact point on the sample, comprising nucleic acids for example.

The size of this area may be set by experimental parameters such as the size of the pump beam at the impact point on the sample, or its modulation frequency, and by the thermal behavior of the support, of the sample and of the ambient medium. This is notably due to heat diffusion in these various media.

As the information is local, the detection unit may be coupled with a system for displacing the solid support relatively to the pump beam. The whole then allows the deviation values of the probe beam to be compared from one point to another of the sample, in particular the signal may be illustrated as a mapping.

A point of the sample may for example, be understood as a molecular recognition area, i.e. a portion of the support which has, at its surface, molecules having a recognition property for a given type of target molecules. The solid support is therefore associated with a sample, itself consisting of several recognition points or areas. The supports are then functionalized supports.

In the case of nucleic acids, each of these recognition areas is associated with only one type of capture molecule which is preferably, but not in a limiting way, different from the other recognition areas which form the same sample. Thus, it is possible either to increase the size of each recognition area, or to have several recognition areas associated with the same kind of capture molecule, and this with the purpose of increasing the signal to be detected.

When the signal is illustrated as a mapping, one then has the measurement of several recognition areas which correspond to several target molecules, either hybridized or not, on the captured molecules.

Further, one or several of these recognition areas may be assigned to one or several calibration samples as mentioned earlier.

When this is required, the deviation signal may be converted into an absorption value, for example via a reference sample or a calibration sample. This reference sample, the absorption of which is known and stable, may be the subject of a photothermal deflection measurement under the same :experimental conditions as for the sample. With the obtained value, it is for example, possible to calculate a coefficient for converting the measured electrical signal into an absorption level.

Finally, when the photothermal method is a thermal lens method, an incident beam is used, which may be a laser beam selected from a 275 nm continuous argon laser, or a quadruple YAG laser with a wavelength of 266 nm.

The thermal lens method is of interest because the assembly is simpler.

Indeed, in this case, there is only one laser which acts as a probe laser and pump laser. After interaction with the sample, the focussing point is changed. The measurement merely consists in measuring the change in light flux at the initial point. The pump beam may be used either in transmission, i.e. through the sample, or in reflection.

The originality of the invention is therefore notably based on the fact that a photothermal technique has never been used for detecting molecular recognition for example of an oligonucleotide hybridization on a solid support. More generally, no method based on the measurement of a change in absorption has been used for this type of detection on a support.

The method of the present invention notably has the advantage of not requiring any labelling step or label. For example, it may advantageously be used for a diagnosis test by detecting hybridization of nucleic acids. This use will be illustrated in the application examples below.

Further, very small absorptions and changes in absorption, for example a few tenths of parts per million, may be detected.

The present invention also relates to a device for implementing the method of the invention, said device comprising the following components:

means for positioning the solid support, means for illuminating said support, means for detecting the absorption of light by the sample borne by the support, when it is illuminated by said illuminating means, and means for positioning said illuminating means and said detecting means.

According to the invention, the means for positioning the support may be any means known for accurately displacing said support, for example micrometric translation and rotation stages, for example of the MicroContrôle trade mark. These means may be motorized so as to notably provide automatization for a mapping.

According to the invention, the means for illuminating the sample and detecting the light absorption by the sample may notably be selected according to the photothermal method used, to the support and to the molecular recognition to be detected. The means for illuminating the sample may be a pump beam, for example, as defined earlier.

When a photothermal deflection method is involved, the means for detecting the absorption may comprise a probe beam and means for detecting refraction or reflection of a probe beam. These means are described below and in the following examples. When a thermal lens method is involved, the detecting means may comprise a probe beam and a diaphragm placed at the focussing point.

According to the invention, the means for positioning the aforementioned illuminating and detecting means may be means such as those mentioned earlier for positioning the support.

Other components of the invention and advantages will further become apparent upon reading the description and the examples which follow with reference to the appended drawings, of course, given as illustrative and non-limiting.

SHORT DESCRIPTION OF THE APPENDIX AND FIGURES

The list of sequences illustrating example 4 is given in the appendix.

EXAMPLES

Example 1

Measurement Method

The system used according to the invention is based on the photothermal deflection in a transverse configuration.

Figure 3:
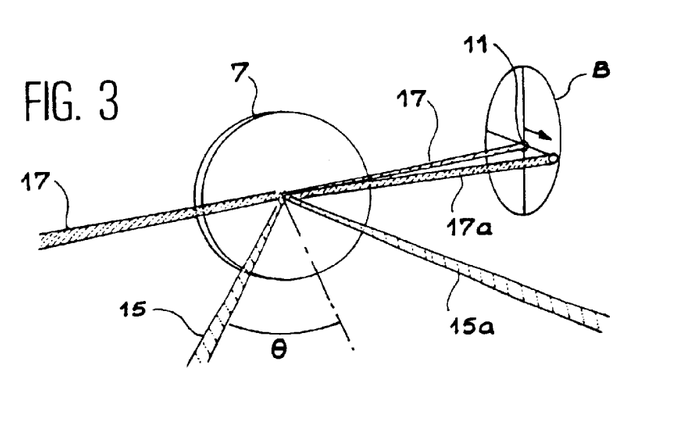
FIG. 3 is a schematic illustration of a measurement of absorption of a sample by the photothermal deflection method according to the invention.

The appended FIG. 3 is a schematic illustration of the principle of a measurement of the absorption of a sample by the photothermal deflection method according to the invention.

In this figure, the pump beam 15 stems from a 275 nm continuous argon laser (COHERENT of the INOVA 40 (trade name) type), it is focussed on sample 7 by means of a spherical mirror (not shown), the spot diameter (not shown) is about 70 microns at the surface of sample 7. The wavelength of the pump beam is selected in order to provide detection of the hybridization of nucleic acids. The power of the pump beam is 300 mW at the laser output.

The probe beam 17 is a beam from a 633 nm helium-neon laser. The wavelength of this probe beam is indifferent. According to the invention, a better signal to noise ratio may be obtained with a wavelength far from that of the pump beam.

Detection of deflection is performed by means of a four quadrant detector -B- (see FIG. 2) followed by amplification and subtraction electronics (not shown). Reference 17a shows, the probe beam deviated by photothermal deflection. The θ angle shows the pump beam's incidence angle with respect to the normal 20 to the sample (shown in mixed lines).

An interference filter (not shown) which selects the wavelength of the probe beam may be placed in front of the four quadrant detector in order to avoid the influence of parasitic light from the modulated pump beam.

In the device of the present invention, the probe laser, the four quadrant detector and the associated electronics may form an integral part of a commercial measurement cell, such as one from ALIS. The signal from this cell is sent to a synchronous detection stage.

The pump beam may be modulated by means of a mechanical slotted disc, also called a mechanical chopper hereafter, the frequency of which is adjustable. The control signal of the chopper is used as a reference for synchronous detection. The frequency is 157 Hz. The measured signal is obtained at the output of the synchronous detection stage (amplitude of the deviation signal at the pump beam's modulation frequency).

The positioning of the sample and of both beams relatively to each other, is provided by translation and rotation stages (Mico-Contrôle trade name), of which some are motorized in order to provide automatization for a mapping, for example of a biochip and in certain adjustment phases. The adjustments are automatically performed in order to maximize the deflection signal in a plane orthogonal to the sample containing the probe beam. During mappings, if required, corrective displacement is performed in a direction orthogonal to the scanning axes for the mapping in order to guarantee that correct relative positioning is maintained during the mapping. This corrective displacement is automatically determined in a preliminary measurement step. The incidence angle of the pump beam with respect to the normal to the sample and the orientation of the cell with respect to the sample may be adjustable. The relative position and orientations of the probe and pump beams may also be adjustable independently.

Figure 4:
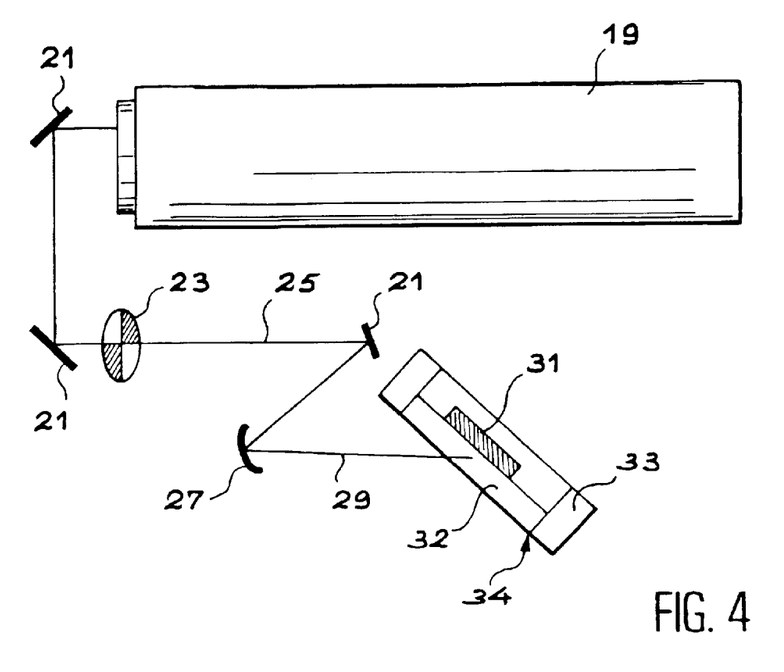
FIG. 4 is a diagram illustrating a device for implementing the method of the present invention.

A diagram of a device according to the invention is illustrated on the appended FIG. 4. In this figure, a shutter, not shown in the diagram, enables the pump beam to be cut off during the displacement phases and to be restored during a well determined time interval after a selected waiting period for allowing the assembly to stabilize after displacement. Reference 19 shows a 275 nm argon laser, reference 21 shows mirrors for positioning the laser beam, reference 23 shows a mechanical chopper, reference 25 the laser beam after its passing through the chopper, reference 27 a focussing mirror and reference 31 the measurement sample.

Reference 34 forms the measurement cell in which are integrated the probe laser 32 and the four quadrant diode 33.

Repeatability of the positioning of the sample may be provided by an autocollimating telescope for example, which is not shown in the diagram. The whole measuring device may be driven by a workstation which controls the displacements and acquires deviation signals in two orthogonal directions.

In this embodiment, the deviation is measured along a direction parallel to the plane of the sample and along a direction orthogonal to the latter. The latter measurement is what forms the useful signal. The electronic signal provided by the synchronous detection stage may be used as such by comparison from one point to another of the sample.

It may also be converted into an absorption value by performing a reference measurement on a sample supposed to be stable over time and under a laser flux, the absorption of which is measurable on the spectrophotdmeter and is located in the linearity range of the photothermal deflection measurement bench.

Example 2

Preparation of Functionalized Supports

The molecules chosen in this example are nucleic acids, in particular oligonucleotides.

The production of thin biological layers to form the measuring sample according to the method of the present invention can for example include two steps:

1) Functionalization of the substrate, and
2) Grafting of the oligonucleotides.

Functionalization of the Substrate

The support chosen is silica. Since the oligonucleotides are not able to establish covalent bonding with this type of material, the latter is functionalized. Functionalization of the support has the goal of modifying the surface of the substrate in order to introduce reactive groups into it that will enable grafting of the oligonucleotides.

This step requires, for example, a first treatment of the support for example by a sulphochromic mixture than silanization. The treatment with the sulphochromic mixture may be carried out by means of a saturated solution of chromium oxide in 95% sulphuric acid. Its objective is to remove organic contaminants present on the support and to create silanol groups. The silanization is then carried out by standard silanization techniques, for example, by incubation of the support in a toluene solution, 1% aminopropyldimethylethoxysilane (AMPMES). During this step, the silanes react with the silanol groups created during the treatment with sulphochromic mixture. The formation of a layer of silane carrying amine groups results from this, on which it is possible to graft oligonucleotides.

Grafting of the Oligonucleotides

The oligonucleotides that form the capture molecules are grafted on the support either directly or through an avidin molecule.

In this latter case, a molecule of avidin is previously grafted on the silane through a coupling agent, phenylene diisothiocyanate (PDC). Avidin presents a strong affinity for a small molecule: biotin. Therefore, it can recognize and very strongly fix an oligonucleotide carrier of a biotin. Therefore, the support is incubated in a solution of 10% dimethylformamide/pyridine 0.2% PDC. After washing and drying the support, avidin is deposited in the form of drops several millimeters in diameter on the support. The carrier oligonucleotide of the biotin is deposited in the same place.

Example 3

Use of Functionalized Supports

This step consists of carrying out hybridization of nucleic acids or fragments of them, which form the target molecules present in the solution to be tested. It consists essentially of two steps:

1) Hybridization of the nucleic acids (in the experiment described, a complementary oligonucleotide), and
2) Washing non hybridized nucleic acids.

Of course, prior to these steps and in the specific case of nucleic acids, it may be required to carry out other preparatory steps to obtain the solution to be tested. These steps may be steps of extraction, amplification and cleavage.

Extraction

This extraction is carried out in an entirely standard manner. In fact, any DNA extraction technique may be used, making it possible to obtain material capable of being amplified later by an amplification procedure. These cell lysis techniques, with extraction, then purification of nucleic acids are usually those recommended for genetic analyses, or rapid techniques using commercial products such as QIAmp Blood Kit (Registered trademark) from QIAGEN S.A.

Amplification

Thus, it may be wise to increase the number of target molecules by amplifying the signal. Very numerous amplification techniques exist. The state of the art describes methods enabling amplification of the nucleotide sequences using specific primers of sequences to be amplified. Thus, a fragment of nucleic acid of interest may be amplified within a preparation of nucleic acids. Numerous techniques use oligonucleotdes complementary to the target sequence acting as primers for elongation by a polymerase.

For amplification of DNA, there is PCR (Polymerase Chain Reaction) such as described in the patents U.S. Pat. No. 4,683,195, U.S. Pat. No. 4,683,202 and U.S. Pat. No. 4,800,159, LCR (Ligase Chain Reaction) explained for example in the patent application EP-A-0.201.184 or the RCR (Repair Chain Reaction) described in the patent application WO-A-90/01069.

For amplification of RNA, several techniques have also been described in different documents. These techniques are the following:

3SR (Self Sustained Sequence Replication) with the patent application WO-A-90/06995, NASBA (Nucleic Acid Sequence-Based Amplification) with the patent application WO-A-91/02818, SPSR (Single Primer Sequence Replication) with the patent U.S. Pat. No. 5,194,370, and TMA (Transcription Mediated Amplification) with the patent U.S. Pat. No. 5,399,491.

Cleavage

Cleavage may also be wise because the product of the amplifications may be formed of nucleic acids that are large in size. Thus, when such target nucleic acids are hybridized on capture molecules, the duplexes formed after hybridization with the target nucleic acids are not very stable. This is also the case when the polynucleotides are used as detection probes. The reasons may be due to the steric inhibition or to the lack of specificity between the capture molecule that is not necessarily of the same size. Therefore, there is going to be a quantitative and qualitative loss of the signal.

The steric inhibition may be, not only because of the length of the nucleic acid, but also the existence or retention of the secondary structures. Cleavage enables these structures to be destroyed and thus optimizes hybridization. This steric inhibition plays a particularly important role n the case of hybridization on the surfaces containing capture probes in high density, for example the DNA chips developed by the Affymetrix company ("Accessing Genetic Information with High-Density DNA arrays", M. Shee et al., Science, 274, 610–614. "Light-generated oligonucleotide arrays for rapid DNA sequence analysis", A. Caviani Pease et al., Proc. Natl.

Sci. USA, 1994, 91, 5022–5026). In this technology, the capture probes are generally of reduced size, around twenty nucleotides.

Where it concerns cleavage of nucleic acids, numerous methods are described in the state of the art. Firstly, cleavage may be enzymatic, that is, the fragmentation of nucleic acids may be carried out by nucleases (DNases or Rnases). Then fragments small in size are created with 3'—OH, 5'—OH, 3'-phosphate, 5'-phosphate ends.

Secondly, cleavage may be chemical. For example, in the case of the DNA, depurination or depyrimidination of the DNA may be carried out, which are then cleaved in the presence of a base by a mechanism called "β-elimination". The cleavage of the DNA may be carried out by mechanisms of oxidation, alkylation, the addition of free radicals, among others. To cleave the RNA, metal cations are used, often combined with organic molecules used as chemical catalysts, for example, imidazole. This cleavage is preferentially carried out in alkaline medium and creates fragments with 3'-phosphate ends.

Hybridization

The support on which the oligonucleotides are grafted is then incubated in a solution containing the complementary oligonucleotide for example a solution of 6×SSPE+0.05% Triton X-100+20 nM target; 30 min at 35° C.

Washing the Nonhybridized Nucleic Acids

After hybridization, the nucleic acids that are not hybridized are removed by washing in the same solution, 6×SSPE+0.05% Triton-X.

Just before the detection according to the method of the present invention, the samples are taken out of their washing solution, passed rapidly under water to remove the buffer while taking care not to "dehybridize" the nucleic acids, and dried in the air.

Results

Mapping is carried out on the sample including two rows of oligonucleotide pins. Each pin is approximately three millimeters in diameter. The pins of the lower row include 32 mer oligonucleotides hybridized by their complementary while those in the upper row include another 32 mer oligonucleotide, not complementary. The mapping step is 250 microns.

The measurement of time is 5 seconds per point including one second before opening the obturator. The measuring point is therefore illuminated for 4 seconds. The measurements are carried out as rapidly as possible during this time. The time delay aimed at between each measurement is a tenth of a second. Therefore, at each measurement point, a signal is provided depending on the time. The speed of the variation of the signal according to time is represented by the curve in the attached FIG. 5.

Figure 5:
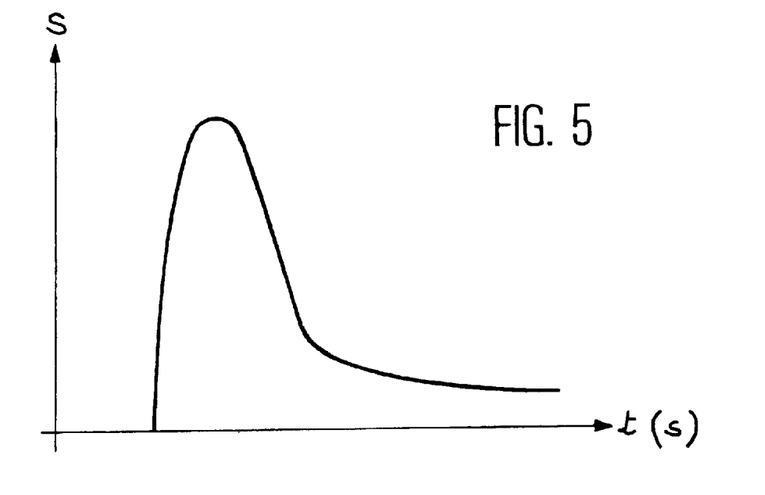
FIG. 5 is a graph illustrating results for the measurement of absorption of a sample consisting of nucleic acids, according to the method of the present invention.

In this figure on the ordinate S represents the signal in absorbance unit and on the abscissa, t represents the time in seconds.

The signal includes a period of background noise, before opening the obturator followed by a rapid increase after opening. When a maximum is reached, the measured signal lowers again, with that expressing the change of the sample at the measuring point. To compare the signals obtained at each point of the mapping, it is preferable to extract from each signal a value that could be displayed in mapping form. This value for example may be the measured maximum or the value at a given time measured. It is also possible to adjust a well-chosen function for each temporal signal and choose as representative value one of the parameters of adjustment of the function or the maximum of the latter. After this treatment phase, the result is displayed in mapping form.

Figure 6:
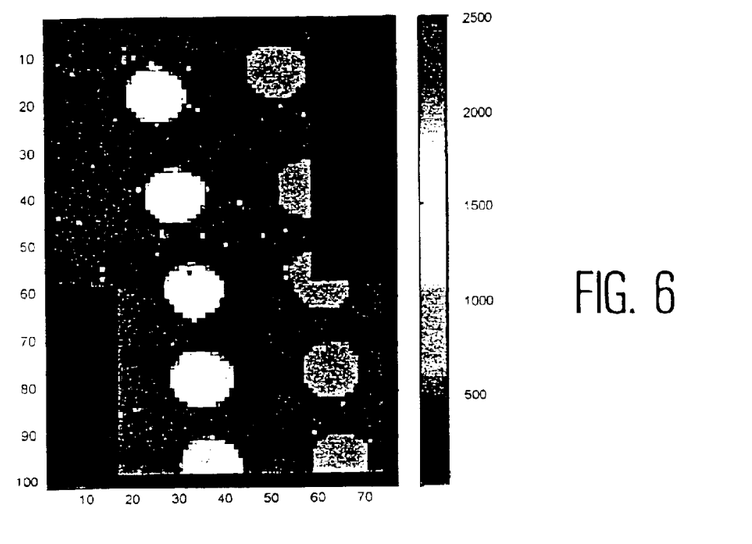
FIG. 6 is a mapping of a detection according to the method of the present invention, performed on a sample including two rows of oligonucleotide pads.

Mapping that we have obtained experimentally is given in FIG. 6 in the annex. It concerns maxima of the signal measured at each point of the mapping, maxima having taken place for t near 1.5 second. On this mapping, the oligonucleotides pins that may or may not be hybridized are perfectly distinguished from the background in which the absorption is very low. The pins of the right column, clear blue in colour on the mapping, have a lower absorption that those of the left column, green to yellow in colour on the mapping; the black rectangles correspond to nonmapped zones, because there had been a manual shift of the support during acquisition of the mapping to better see the pins of the right column. The observation of the mapping is therefore sufficient to determine if an oligonucleotide pin is hybridized or not.

Figure 7A:
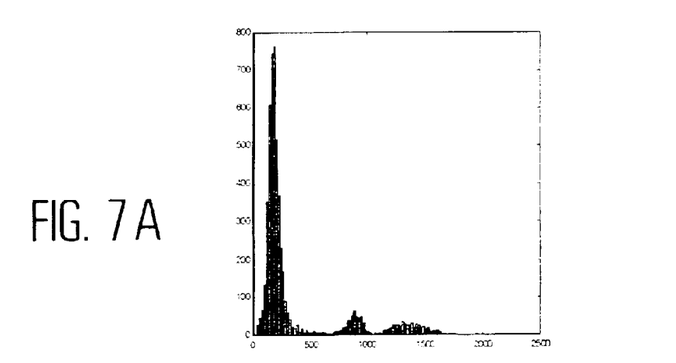
FIGS. 7a and 7b are histograms which represent the number of pixels of the mapping of FIG. 6.
Figure 7B:
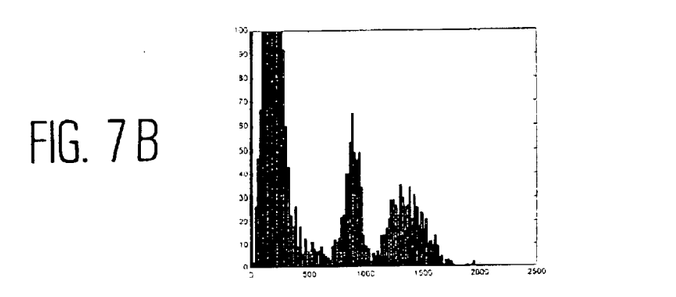

Histograms of FIGS. 7a and 7b in the annex represent the number of pixels of the mapping (ordinate axis) for a given signal intensity (abscissa axis) on two different scales for the ordinates. Three modes are clearly seen to appear, corresponding to the absorption of the background, nonhybridized oligonucleotides, and hybridized oligonucleotides. These modes are well separated which enables use of image treatment methods enabling automatic recognition of the pins that may or may not be hybridized. A simple thresholding for example, makes it possible to only retain the hybridized pins and some absorbing points easily distinguished from measuring pins.

Example 4

Diagnostic Test

An important part of the genetic component of the susceptibility to rheumatoid arthritis was able to be associated with the HLA-DRB genes, coding for the b chain of the HLA-DR molecules involved in the presentation of the peptides to the T lymphocytes, pivotal function at the core of mechanisms of regulation of the immune response. More precisely, it has been shown that the presence of a specific sequence of five amino acids, corresponding to positions 70 to 74 of the third hypervariable region of the HLA-DRb1 molecules, was found for different alleles reported as being associated with rheumatoid arthritis. The involvement of this "shared epitope" corresponding to sequences QKRAA or QRRAA or RRRAA (code with a letter for the amino acids) is from then on well documented.

However, if this group of DRB1*04 alleles is associated with rheumatoid arthritis, all the alleles currently known (DRB1*0401 to DRB1*0427) are not necessarily associated with this disease. A result of this may be that if it is limited to a typing of the group of DRB1*04 alleles according to the alleles present, one could obtain, beside true positives or true negatives, false positives which are going to unnecessarily alarm the physician and the patient.

In the case of a molecular biology technique (analysis of DRB1 alleles: results rendered according to the DRB1*01 to DRB1*10 nomenclature); the clinician is essentially interested in the presence of the DRB1*04 allele(s).

In case of results suggesting a predisposition to the disease, a second test is generally made using a molecular biology technique known as high resolution, known as subtyping of DR4, to clarify the DRB1*04 allele (DRB1*0401 to 0427 according to the official nomenclature in 1998), only the DRB1*0401, 0404, 0405 and 0408 being reported as being associated with the disease.

Extraction

Extraction is carried out by commercial products mentioned previously, such as QIAmp Blood Kit (registered trademark) of QIAGEN S.A.

Amplification

This amplification concerns the HLA-DR locus including the region of the exon 2 which corresponds to the codons 5 to 94 according to the official nomenclature of the HLA-DRB genes. Table 1 below describes the primers used during amplification by PCR of this previously described locus. It also gives all the physicochemical positions enabling this amplification to be made.

TABLE 1

Simultaneous amplification of the HLA-DR region of interest

| Primers | P1 (5'-DR primer): CCG GAT CCT TCG TGT CCC CAC AGC ACG (5'>3') (SEQ ID NO: 16) |
| | P2 (3'-DR primer): TCG CCG CTG CAC TGT GAA G (5'>3') (SEQ ID NO: 17) |
| Reaction mixture | buffer 10× TEMAG(*): 10 µL |
| | dNTPs (20 mM): 1 µL (0.2 mM final) |
| | P1 (30 µM): 0.8 µL (0.25 µM final) |
| | P2 (30 µM): 0.8 µL (0.25 µM final) |
| | AmpliTaq (5 U/µL): 0.5 µL (2.5 U) |
| | DNA: 100–500 ng |
| | H2O: QSP 100 µL |
| Amplification programme | (5 min at 96° C.) + 10 × (10 sec at 98° C. + 30 sec at 65° C. + 30 sec at 72° C.) + 30 × (20 sec at 96° C. + 30 sec at 65° C. + 30 sec at 72° C.) |

(*)Buffer 10× TEMAG: 500 mM Tris-HCl pH 8.8, 150 mM ammonium sulphate, 15 mM MgCl2, 500 µM EDTA, 0.1% gelatine In this example the distance separating the two sources P1 and P2 is chosen to be sufficiently short so as not to have cleavage carried out. Of course, if the amplicons produced require it, this fragmentation of the nucleic acids may be carried out according to the means and conditions explained above.

Preparation of the Functionalized Supports

To be able to make a study of genetic predisposition to rheumatoid arthritis, there is reason to use a group of hybridization reactions using a set of oligonucleotide probes enabling the precise analysis of HLA-DRB1 and HLA-B*27 alleles or groups of alleles. Table 2 describes the group of probes that is used for detection of these two diseases. The instructions that are given from the left to the right are the following:

the reference of the assigned probe in HLA nomenclature,
the assigned number of the sequence in this document,
the HLA gene concerned,
the sequence forming this probe, and
the localization of the codons (three nucleotides) on the HLA genes.

TABLE 2

Oligonucleotide probes

| Probe | SEQ ID NO | HLA gene | Sequence (5'>3') | Localization (codons) |
|---|---|---|---|---|
| C+ | 1 | DR | TTC GAC AGC GAC GTG GGG (SEQ ID NO: 1) | 40–45 |
| C− | 2 | — | TAT GAA ACT TAT GGG GAT AC (SEQ ID NO: 2) | — |
| 4 | 3 | DR | GAT ACT TCT ATC ACC A (SEQ ID NO: 3) | 29–34 |
| QK71 | 4 | DR | GAG CAG AAI CGG ICC (SEQ ID NO: 4) | 69–73 |
| | | | *GAG CAG AAG CGG GCC* (SEQ ID NO: 18) | |
| IDE71 | 5 | DR | CTG GAA GAC GAI CGG (SEQ ID NO: 5) | 68–72 |
| | | | *CTG GAA GAC GAG CGG* (SEQ ID NO: 19) | |
| E74 | 6 | DR | AGC AIA IGC IGG ICI AII (SEQ ID NO: 6) | 69–75 |
| | | | *AGC AGA GGC GGG CCG AGG* (SEQ ID NO: 20) | |
| QR71 | 7 | DR | CAG AGG CGI GII ICI GTG (SEQ ID NO: 7) | 70–75 |
| | | | *CAG AGG CGG GCC GCG GTG* (SEQ ID NO: 21) | |
| S57 | 8 | DR | GCC TAG CGC CGA GTA (SEQ ID NO: 8) | 55–60 |
| 1 | 9 | DR | TGG CAG CTT AAG TTT GAA (SEQ ID NO: 9) | 9–14 |
| 52 | 10 | DR | TAC TCT ACG TCT GAG T (SEQ ID NO: 10) | 10–15 |
| 2 | 11 | DR | CAG CCT AAG AGG GAG TG (SEQ ID NO: 11) | 10–15 |
| 7 + 9 | 12 | DR | IAG GTI GAC AIC GTG TGC (SEQ ID NO: 12) | 74–79 |
| | | | *CAG GTG GAC ACC GTG TGC* (SEQ ID NO: 22) | |
| 10 | 13 | DR | GGA GGA GGT TAA GTT (SEQ ID NO: 13) | 8–13 |
| 8 + 12 | 14 | DR | CTC TAC GGG IGA GT (SEQ ID NO: 14) | 10–15 |
| | | | *CTC TAC GGG TGA GT* (SEQ ID NO: 23) | |
| 3 | 15 | DR | CCG GGT GGA CAA CIA C (SEQ ID NO: 15) | 73–78 |
| | | | *CCG GGT GGA CAA CTA C* (SEQ ID NO: 24) | |

For certain probes, a second sequence in italics specifies the natural sequence, that is, only formed from four nucleotides adenosine (A), thymine (T), guanine (G) and cytosine (C). The other sequences have the same nucleotides except for the substitution of certain ones by different nucleotides. In the present case, it is inosine. The use of the inosines enables improvement again of the specificity of the probes with respect to the sequences with which they are going to be hybridized. The specificity of the capture probes is clearly specified in Table 3 below.

TABLE 3

Principal specificities of the molecules or capture probes

| Probe | SEQ ID NO | Specificity |
|---|---|---|
| C+ | 1 | All the DRB1* |
| C− | 2 | None |
| 4 | 3 | DRB1*04 |

TABLE 3-continued

Principal specificities of the molecules or capture probes

| Probe | SEQ ID NO | Specificity |
|---|---|---|
| QK71 | 4 | DRB1*04 allele possessing the QKRAA unit corresponding to the shared epitope |
| IDE71 | 5 | DRB1*0402 |
| E74 | 6 | DRB1*0403, 0406 and 0407 |
| QR71 | 7 | DRB1*0101, 0404, 0405, 0408 and 1402 allele possessing the unit QRRAA corresponding to the shared epitope |
| S57 | 8 | DRB1*0405 |
| 1 | 9 | DRB1*01 |
| 52 | 10 | DRB1*03, 11, 13 and 14 |
| 2 | 11 | DRB1*02 |
| 7 + 9 | 12 | DRB1*07 and 09 |
| 10 | 13 | DRB1*10 |
| 3 | 14 | DRB1*03 |
| 8 + 12 | 15 | DRB1*08 and 12 |

These probes are next set up on the solid support as mentioned previously. Of course, to facilitate the later analysis, it is appropriate to position each type of probe on a point or recognition zone.

In the present case, fifteen different recognition zones are required, by including the controls, whether they are positive or negative. It is also possible to carry out other tests on the same solid support, for that it is sufficient to increase the number of recognition zones.

TABLE 4

Organization of the different recognition zones on the solid support

Recognition zones

| | |
|---|---|
| C+ | SEQ ID NO 1 |
| C− | SEQ ID NO 2 |
| 4 | SEQ ID NO 3 |
| QK71 | SEQ ID NO 4 |
| IDE71 | SEQ ID NO 5 |
| E74 | SEQ ID NO 6 |
| QR71 | SEQ ID NO 7 |
| S57 | SEQ ID NO 8 |
| 1 | SEQ ID NO 9 |
| 52 | SEQ ID NO 10 |
| 2 | SEQ ID NO 11 |
| 7 | SEQ ID NO 12 |
| 10 | SEQ ID NO 13 |
| 8 + 12 | SEQ ID NO 14 |
| 3 | SEQ ID NO 15 |

There is a positive control (SEQ ID NO 1) which enables detection of all the alleles of the DRB1* gene, which makes it possible to check that the amplification has clearly concerned the region of interest between the primers P1 and P2 described in Table 1. The negative control (SEQ ID NO 2) has no diagnostic objective. It is present only to fulfil certain standards. This sequence is absolutely not specific to HLA and corresponds to a random sequence not found in the HLA genes.

The SEQ ID NO 3 enables the typing of all the alleles that form the DRB1*04 group. It enables the identification of all the DRB1*04 alleles, alleles belonging to the group defined as group DR4 by the HLA typing techniques by serology. It concerns a probe with low resolution, that is, that numerous alleles may be recognized by the latter.

As for the SEQ ID NO 4 to 8, they enable subtyping of some of the alleles which form the DRB1*04 group, by specifying the allele(s) sharing a particular sequence. It concerns probes with high resolution, that is, that some alleles, even only one, may be recognized by these probes.

All these probes are used for detecting the alleles possessing the shared epitope associated with the genetic predisposition to rheumatoid arthritis. More specifically, the probes SEQ ID NO 4 and 7 enable detection of the alleles associated with the susceptibility to rheumatoid arthritis, and the probes SEQ ID NO 5 and 6 enable detection of the alleles associated with the resistance to said rheumatoid arthritis. The probe SEQ ID NO 8 enables confirmation of a DRB1*0405 allele.

Results

In the results explained below, we worked with solutions to be tested for which the characteristics were known, in order to be able to check if the results obtained with the analysis method according to the present invention are clearly in conformance with reality.

$1^{ST}$ Solution to be Tested

Table 5 which follows shows the signal values obtained with the first solution to be tested in which we had subtracted the value of the signal of the probe SEQ ID NO 2 (negative control). These values more or less far from the zero value make it possible to deduce whether hybridization has taken place or not. The 0 value has been put for all values not being distinguished significantly from the value obtained for SEQ ID NO 2 (deviation less than 2 times the standard error at the mean calculated for the probe SEQ ID NO 2).

TABLE 5

Hybridization results obtained with the first solution to be tested

| Probe associated with the recognition zone | Signal (arbitrary unit) | +/− |
|---|---|---|
| SEQ ID NO 1 | 3000 | + |
| SEQ ID NO 2 | 0 | − |
| SEQ ID NO 3 | 920 | + |
| SEQ ID NO 4 | 260 | + |
| SEQ ID NO 5 | 0 | − |
| SEQ ID NO 6 | 0 | − |
| SEQ ID NO 7 | 0 | − |
| SEQ ID NO 8 | 0 | − |
| SEQ ID NO 9 | 0 | − |
| SEQ ID NO 10 | 0 | − |
| SEQ ID NO 11 | 2100 | + |
| SEQ ID NO 12 | 0 | − |
| SEQ ID NO 13 | 0 | − |
| SEQ ID NO 14 | 0 | − |
| SEQ ID NO 15 | 0 | − |

The analysis of the HLA-DR shows that:
- the SEQ ID NO 1 probe is positive: the HLA-DR amplification test and the hybridization test worked well,
- the probes SEQ ID NO 3 and SEQ ID NO 4 are positive: a DRB1*0401 allele is present, and
- the probe SEQ ID NO 11 is positive: a DRB1*02 allele is present.

In conclusion, there an allele of susceptibility for rheumatoid arthritis (DRB1*0401) is present, the second allele being DRB1*02 which was proof of neutrality with respect to rheumatoid arthritis.

The HLA typing of the first sample was HLA-DRB1*0401/1602.

$2^{ND}$ Solution to be Tested

Table 6 which follows, shows the values of OD obtained with the second sample to be tested.

TABLE 6

Results of hybridization obtained with the second solution to be tested

| Probe associated with the recognition zone | Signal (arbitrary unit) | +/− |
|---|---|---|
| SEQ ID NO 1 | 3000 | + |
| SEQ ID NO 2 | 0 | − |
| SEQ ID NO 3 | 310 | + |
| SEQ ID NO 4 | 0 | − |
| SEQ ID NO 5 | 370 | + |
| SEQ ID NO 6 | 0 | − |
| SEQ ID NO 7 | 0 | − |
| SEQ ID NO 8 | 0 | − |
| SEQ ID NO 9 | 0 | − |
| SEQ ID NO 10 | 0 | − |
| SEQ ID NO 11 | 2700 | + |
| SEQ ID NO 12 | 0 | − |
| SEQ ID NO 13 | 0 | − |
| SEQ ID NO 14 | 0 | − |
| SEQ ID NO 15 | 0 | − |

There are four positive probes, which are:

the SEQ ID NO 1 probe: the HLA-DR amplification and the hybridization test worked well the probe SEQ ID NO 3: at least a DRB1*0401 allele is present the probe SEQ ID NO5: at least a DRB1*0402 allele is present, and the probe SEQ ID NO 11: at least a DRB1*02 allele is present Therefore, it concerns two DR4 alleles not involved in the genetic susceptibility to rheumatoid arthritis, DRB1*0402 and DRB1*02.

The HLA typing of this third sample was HLA-DRB1*0402/02.

References

Doc. 1:
Balladur, V., Theretz, A., and Mandrand, B. Determination of the Main Forces Driving DNA Oligonucleotide Adsorption onto Aminated Silica Wafers. *J. Colloid Interface Sci* 194 (2): 408–418, 1997.

Doc. 2:
Cornell, B. A., Braach-Maksvytis, V. L. B., King, L. G ., Osman, P. D. J., Raguse, B., Wieczorek, L., and Pace, R. J. A biosensor that uses ion-channel switches. *Nature* 387: 580–583, 1997.

Doc. 3:
Elaissari, A., Cros, P., Pichot, C., Laurent V., and Mandrand, B. Adsorption of oligonucleotides onto negatively and positively charged latex particles. *Colloids and Surfaces* 83: 25–31, 1994.

Doc. 4:
Guc, Z., Guilfoyle, A., Thiel, A. J., Wang, R., and Smith, L. M. Direct fluorescence analysis of genetic polymorphisms by hybridization with oligonucleotide arrays on glass supports. *Nucl. Acids Res.* 22 (24): 5456–5465, 1994.

Doc. 5:
Kohsaka, H., Taniguchi, A., Richman, D. D., and Carson, D. A. Microtiter format gene quantification by covalent capture of competitive PCR products: application to HIV-1 detection. *Nucl. Acids Res.* 21(15):3469–3472, 1993.

Doc. 6:
Maskos, U. and Southern, E. M. Oligonucleotide hybridisations on glass supports: a novel linker for oligonucleotide synthesis and hybridization properties of oligonucleotides synthesized in situ. *Nucl. Acids Res.* 20(7):1679–1684, 1992.

Doc. 7:
Matson, R. S., Rampal, J. B., and Coassin, P. J. Biopolymer synthesis on polypropylene supports—I. Oligonucleotides. *Analytical Biochemistry* 217:306–310, 1994.

Doc. 8:
Noy, A., Vezenov, D. V., Kayyem, J. F., Meade, T. J., and Lieber, C. M. Stretching and breaking duplex DNA by chemical force microscopy. *Chem. Biol.* 4 (7):519–527, 1997.

Doc. 9:
Pease, A. C., Solas, D., Sullivan, E. J., Cronin, M. T., Holmes, C. P., and Fodor, S. D. Light-generated oligonucleotide arrays for rapid DNA sequence analysis. *Proceedings of the National Academy of Sciences USA* 91:5022–5026, 1994.

Doc. 10: Porath, J., Carlsson, J., Olsson, T., and Belfrage, G. Metal chelate affinity chromatography, a new approach to protein fractionation. *Nature* 258(5536):598–599, 1975.

What is claimed is:

1. A detection method, comprising:
   detecting of a molecular recognition reaction between a first molecule fixed on a support and a second molecule present in a solution to be tested, without labeling the first and second molecule, in which the detection is made by a photothermal method.

2. The detection method, without labelling, of a molecular recognition reaction according to claim 1, which is a hybridization reaction of nucleic acids said method comprising:
   fixing of the first nucleic acid molecule on a solid support,
   contacting of the first nucleic acid molecule fixed on the solid support with a solution to be tested suspected of containing the second nucleic acid molecule, said second molecule being capable of being hybridized with said first molecule, the contacting being carried out under conditions favorable for said hybridization,
   washing of the solid support to isolate a detection sample formed from said first molecule fixed on the support and possibly said second molecule hybridized on said first molecule, and
   measuring the absorption of the sample by a photothermal method.

3. The detection method according to claim 1 in which the photothermal method is a thermal lens method.

4. The detection method according to claim 2 in which the photothermal method is a thermal lens method.

5. The detection method according to claim 1 in which the photothermal method is a method of photothermal deflection in which the sample is illuminated by a pump beam and the absorption of the pump beam by a sample is detected by the refraction or the reflection of a probe beam.

6. The detection method according to claim 2 in which the photothermal method is a method of photothermal deflection in which the sample is illuminated by a pump beam and the absorption of the pump beam by a sample is detected by the refraction or the reflection of a probe beam.

7. The detection method according to claim 5 in which the probe and pump beams cross each other.

8. The detection method according to claim 6 in which the probe and pump beams cross each other.

9. The detection method according to claim 5 in which the probe and pump beams are in a transverse configuration or in an approximately collinear configuration.

10. The detection method according to claim 6 in which the probe and pump beams are in a transverse configuration or in an approximately collinear configuration.

11. The detection method according to claim 5 in which the pump bean is chosen from a pulsed laser, a continuous intensity modulated laser or polychromatic light.

12. The detection method according to claim 5 in which the refraction or the reflection of the probe beam is detected by means of multi-element photodiode or by means of a simple photodiode receiving only part of the probe bean.

13. The detection method according to claim 11 in which the refraction or the reflection of the probe beam is detected by means of multi-element photodiode or by means of a simple photodiode receiving only part of the probe beam.

14. The detection method according to claim 5 in which the pump beam is a beam from a laser chosen from a continuous argon laser at 275 nm, a quadrupled YAG laser with a wavelength of 266 nm or a polychromatic light.

15. The detection method according to claim 5 in which the probe beam has a wavelength that is not absorbed by the substrate nor the present molecules.

16. The detection method according to claim 3 in which an incident beam is used, said beam being a beam from a laser chosen from a continuous argon laser at 275 nm, a quadrupled YAG laser with a wavelength of 266 nm or polychromatic light.

17. The detection method according to claim 4, comprising in addition a step for comparing the measurement of absorption of the sample with that of a control sample.

18. The method according to claim 1 in which hybridization of nucleic acids is detected.

19. The method according to claim 2 in which hybridization of nucleic acids is detected.

20. The detection method according to claim 6 in which the pump bean is chosen from a pulsed laser, a continuous intensity modulated laser or polychromatic light.

21. The detection method according to claim 6 in which the refraction or the reflection of the probe beam is detected by means of multi-element photodiode or by means of a simple photodiode receiving only part of the probe beam.

22. The detection method according to claim 20 in which the pump bean is chosen from a pulsed laser, a continuous intensity modulated laser or polychromatic light.

23. The detection method according to claim 6 in which the pump beam is a beam from a laser chosen from a continuous argon laser at 275 nm, a quadrupled YAG laser with a wavelength of 266 nm or a polychromatic light.

24. The detection method according to claim 6 in which the probe beam has a wavelength that is not absorbed by the substrate nor the present molecules.

25. The method according to claim 11 in which hybridization of nucleic acids is detected.

26. A detection method, comprising:

detecting a molecular recognition reaction between a first molecule fixed on a support and a second molecule present in a solution to be tested, without labeling said first and said second molecule, in which the detection is made by a photothermal method;

wherein said molecular recognition reaction is a hybridization reaction of nucleic acids, said method comprising:

fixing of the first nucleic acid molecule on a solid support;

contacting of the first nucleic acid molecule fixed on the solid support with a solution to be tested suspected of containing the second nucleic acid molecule, said second molecule being capable of being hybridized with said first molecule, the contacting being carried out under conditions favorable for said hybridization;

washing fixed on the support to isolate a detection sample formed from said first molecule fixed on the support and possibly said second molecule hybridized on said first molecule; and measuring the absorption of the sample by a photothermal method.

* * * * *